United States Patent [19]

Kralovic et al.

[11] Patent Number: 5,077,008
[45] Date of Patent: Dec. 31, 1991

[54] ANTI-MICROBIAL COMPOSITION

[75] Inventors: Raymond C. Kralovic, Springfield, Pa.; Duncan C. Badertscher, Cleveland, Ohio

[73] Assignee: Steris Corporation, Painesville, Ohio

[21] Appl. No.: 229,917

[22] Filed: Aug. 8, 1988

Related U.S. Application Data

[63] Continuation-in-part of Ser. No. 140,388, Jan. 4, 1988, and a continuation-in-part of Ser. No. 165,189, Mar. 7, 1988, each is a continuation-in-part of Ser. No. 826,730, Feb. 6, 1986, Pat. No. 4,731,222.

[51] Int. Cl.$^5$ ............................................. A61L 2/18
[52] U.S. Cl. ...................................... 422/37; 252/95; 252/106; 252/389.2; 252/389.4; 252/389.5; 252/389.54; 422/16; 422/18; 422/28
[58] Field of Search .................. 422/16, 18, 28, 37, 422/119; 252/95, 106, 389.2, 389.4, 389.5, 389.54

[56] References Cited

U.S. PATENT DOCUMENTS

| | | | |
|---|---|---|---|
| 2,618,605 | 11/1952 | Schaeffer | 252/137 |
| 2,618,606 | 11/1952 | Schaeffer | 252/137 |
| 2,618,607 | 11/1952 | Sanders | 252/137 |
| 2,618,608 | 11/1952 | Schaeffer | 253/137 |
| 3,684,477 | 8/1972 | Blumbergs et al. | 71/67 |
| 3,864,271 | 2/1975 | Stalter | 252/99 |
| 3,907,991 | 9/1975 | Accetta | 424/130 |
| 4,051,058 | 9/1977 | Bowing et al. | 252/186 |
| 4,051,059 | 9/1977 | Bowing et al. | 252/186 |
| 4,237,090 | 12/1980 | DeMonbrun et al. | 422/13 |
| 4,518,585 | 5/1985 | Greene et al. | 424/130 |
| 4,721,123 | 1/1988 | Cosentino et al. | 134/57 |
| 4,752,444 | 6/1988 | Bowen et al. | 422/28 |
| 4,772,413 | 9/1988 | Massaux et al. | 252/174.21 X |

OTHER PUBLICATIONS

Japanese Patent Abstract 82174Y/46 of Tokyo Shibaura Electric Ltd. "Removal of Slime in Metal Water Pipes—by passing through an . . . ".
Chemical Abstract No. 64532w, vol. 83, No. 8, Aug. 1975, p. 385 "Attempts to reduce peracetic acid corrosion of iron, copper, . . . ".
Chemical Abstract No. 52264d, vol. 93, No. 6, Aug. 1980, p. 353 "Further studies on the protection of metals against the corrosive action . . . ".
Technical Literature for PROXITANE 1507.
Technical Bulletin for Peracetic Acid, 35%, FMC.

*Primary Examiner*—Jill Johnston
*Attorney, Agent, or Firm*—Fay, Sharpe, Beall, Fagan, Minnich & McKee

[57] ABSTRACT

Medical instruments, which may include brass, copper, aluminum, stainless steel, carbon steel, or plastic parts are sterilized or disinfected in an anti-microbial solution. The anti-microbial effect of a strong oxidizing agent, such as peracetic acid, is improved with a wetting agent. The solution further includes a triazole or other component for inhibiting the corrosion of copper and brass. Phosphates or other buffering agents adjust the oxidizing agent generally to a neutral pH for preventing the corrosion of steel. Molybdates or analogous compounds also buffer the pH and inhibit corrosion of aluminum by the oxidizing agent. The corrosion inhibiting is enhanced by the wetting agent. Optionally, a sequestering agent is provided for inhibiting hard water precipitation.

19 Claims, 2 Drawing Sheets

ANTI-MICROBIAL COMPOSITION

BACKGROUND OF THE INVENTION

This application is a continuation-in-part of U.S. application Ser. No. 140,388, filed Jan. 4, 1988, and Ser. No. 165,189, filed Mar. 7, 1988, which in turn are continuations-in-part of application Ser. No. 826,730, filed Feb. 6, 1986, now U.S. Pat. No. 4,731,222.

The present invention relates to anti-microbial solutions. It finds particular application in conjunction with automated sterilizing or disinfecting of medical instruments and will be described with particular reference thereto. However, it is to be appreciated that the present invention will find utility in sterilizing and disinfecting a wide range of objects, either automatically or manually.

Heretofore, most medical instruments have been sterilized in a steam autoclave. In hospitals and large facilities, medical instruments and equipment were transported to a central sterilizing facility where they were sterilized under the supervision of sterilizing room technicians. In a steam autoclave, the equipment was subject to superheated steam at high pressures, depressurized, and cooled. One of the drawbacks of the steam autoclave is that many medical instruments cannot withstand the high temperatures and pressures. Another drawback resides in the one to two hour cycle time.

Instruments and equipment which could not withstand the pressure or temperature of the autoclave were commonly sterilized with ethylene oxide gas. The equipment was sealed in a sterilizing chamber which was pressurized with the ethylene oxide gas. After an appropriate sterilizing cycle, the equipment was degassed for twelve to sixteen hours in a vacuum or about 72 hours in ambient atmospheric conditions to remove the highly toxic ethylene oxide. One of the drawbacks to ethylene oxide sterilization resided in the long cycle times. Another drawback resided in the need for training technicians to handle the highly toxic ethylene oxide gas systems. Yet another drawback was that some medical equipment could not be sterilized with ethylene oxide gas.

Liquid sterilization systems were utilized for equipment which could not withstand either the autoclave or the ethylene oxide. The equipment was immersed in a vat or tank that had been filled with a sterilizing solution, such as stabilized hydrogen peroxide or glutaraldehyde. Because such liquid sterilizations were normally performed manually, the skill and care of the technician were controlling factors in whether sterilization or disinfection were, in fact, attained. In many instances, the technician was required to mix the components of the anti-microbial composition. Even when mixed properly, relatively long immersion times on the order of six to ten hours were commonly required to assure sterilization. Moreover, many liquid sterilization systems were highly corrosive to metal parts, particularly brass, copper, and aluminum. With long immersion times, even carbon steel and stainless steel could be pitted and sharp cutting edges dulled.

In accordance with the present invention, a new and improved anti-microbial composition is provided which overcomes the above referenced problems and others.

SUMMARY OF THE INVENTION

In accordance with one aspect of the present invention, an anti-microbial solution is provided which comprises an oxidizing anti-microbial agent, a copper and brass corrosion inhibitor, an aluminum corrosion inhibitor, a steel corrosion inhibitor and buffering agent, and a wetting agent. If tap water is used as a dilutant, a sequestering agent is also provided.

In accordance with one more limited aspect of the invention, the oxidizing anti-microbial agent is selected from the class consisting of ozone, peracetic acid, organic peroxides, hydrogen peroxides, inorganic peroxides, and other oxygen releasing compounds, chlorine, chlorine dioxide, active chlorine releasing compounds, such as chloramines, hypochlorites, and phenol. Peracetic acid in a range of 0.005%–1.0% is preferred.

In accordance with another more limited aspect of the invention, the copper and brass corrosion inhibitor is selected from the class consisting essentially of triazoles, azoles, benzoates, and five membered ring compounds. Triazoles, particularly benzotriazole and tolytriazole, are preferred.

In accordance with another more limited aspect of the invention, the aluminum and steel corrosion inhibitor and the buffering agent were selected from the class consisting essentially of chromates, dichromates, borates, phosphates, molybdates, vanadates, and tungsdates. More specifically to the preferred embodiment, phosphates are preferred of inhibiting steel corrosion and buffering the solution to a substantial pH. Molybdates are preferred for inhibiting aluminum corrosion.

In accordance with a more limited aspect of the invention, a method of sterilizing medical instruments is provided. Powdered water soluble reagents including a copper and brass corrosion inhibitor, an anti-corrosive buffering agent, a sequestering agent, and a wetting agent are dissolved in water and circulated through the plumbing of an automated sterilizing apparatus and over the medical instruments to be sterilized. A concentrated, oxidizing anti-microbial agent is diluted into the water with dissolved powder reagents and circulated through the plumbing of the automated apparatus and over the medical instruments. After the diluted anti-microbial has remained in contact with the medical instrument for a selected duration, the anti-microbial solution is drained and the medical instrument is rinsed with sterilized water.

In accordance with a more limited aspect of the sterilizing method, the reagents are selected from the classes discussed above.

One advantage of the present invention is that it provides an anti-microbial agent which quickly sterilizes or disinfects medical equipment or the like.

Another advantage of the present invention is that it works on substantially all materials with minimal corrosion.

Yet another advantage of the present invention is that it facilitates automated sterilizing and minimizes operator error.

Still further advantages of the present invention will become apparent upon reading and understanding the following detailed description.

BRIEF DESCRIPTION OF THE DRAWINGS

The invention may take form in various components and arrangements of components or in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
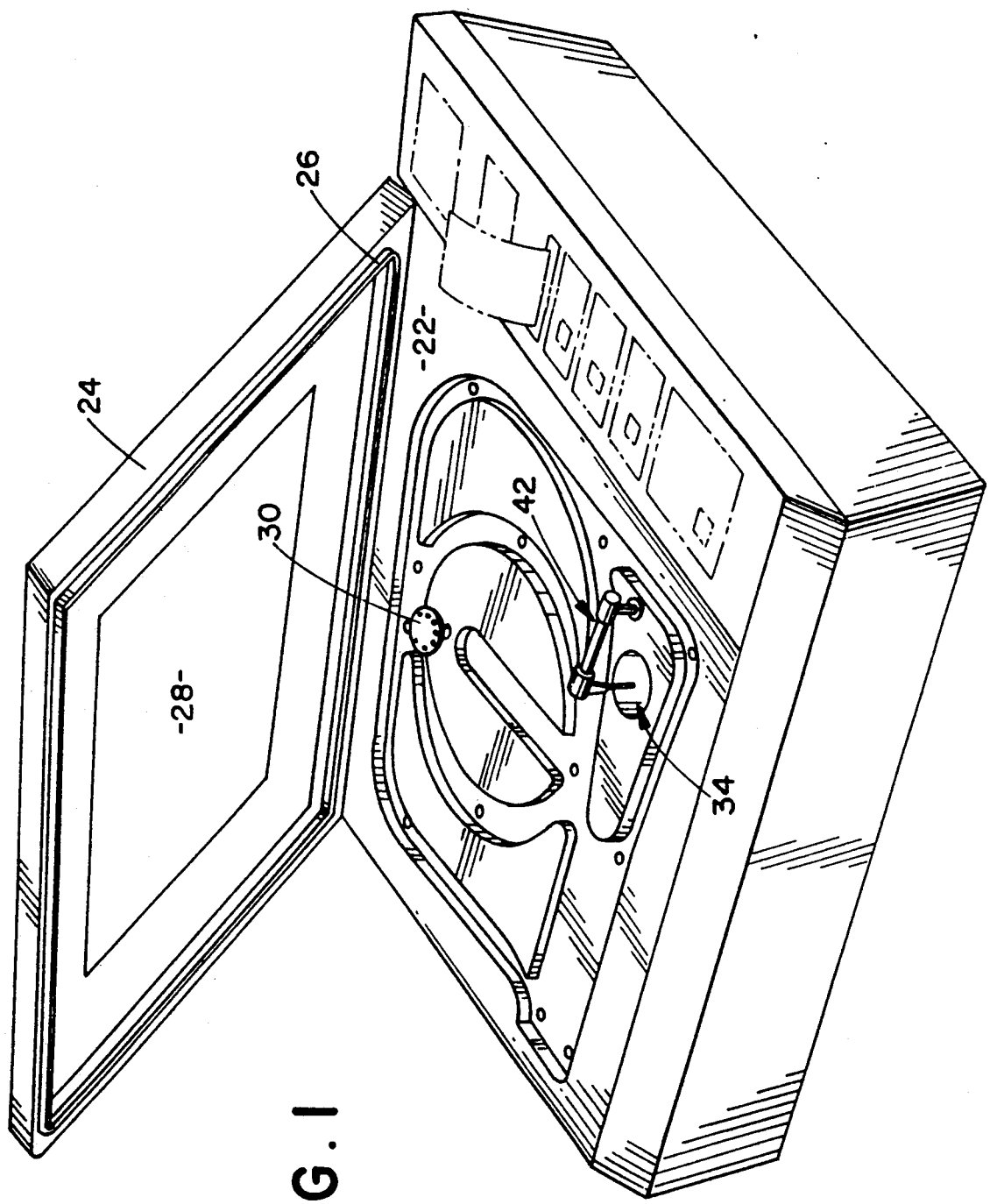
FIG. 1 is a perspective view of a sterilizing apparatus in accordance with the present invention; and, FIG. 2 is a tubing diagram of the sterilizer of FIG 1.
Figure 2:
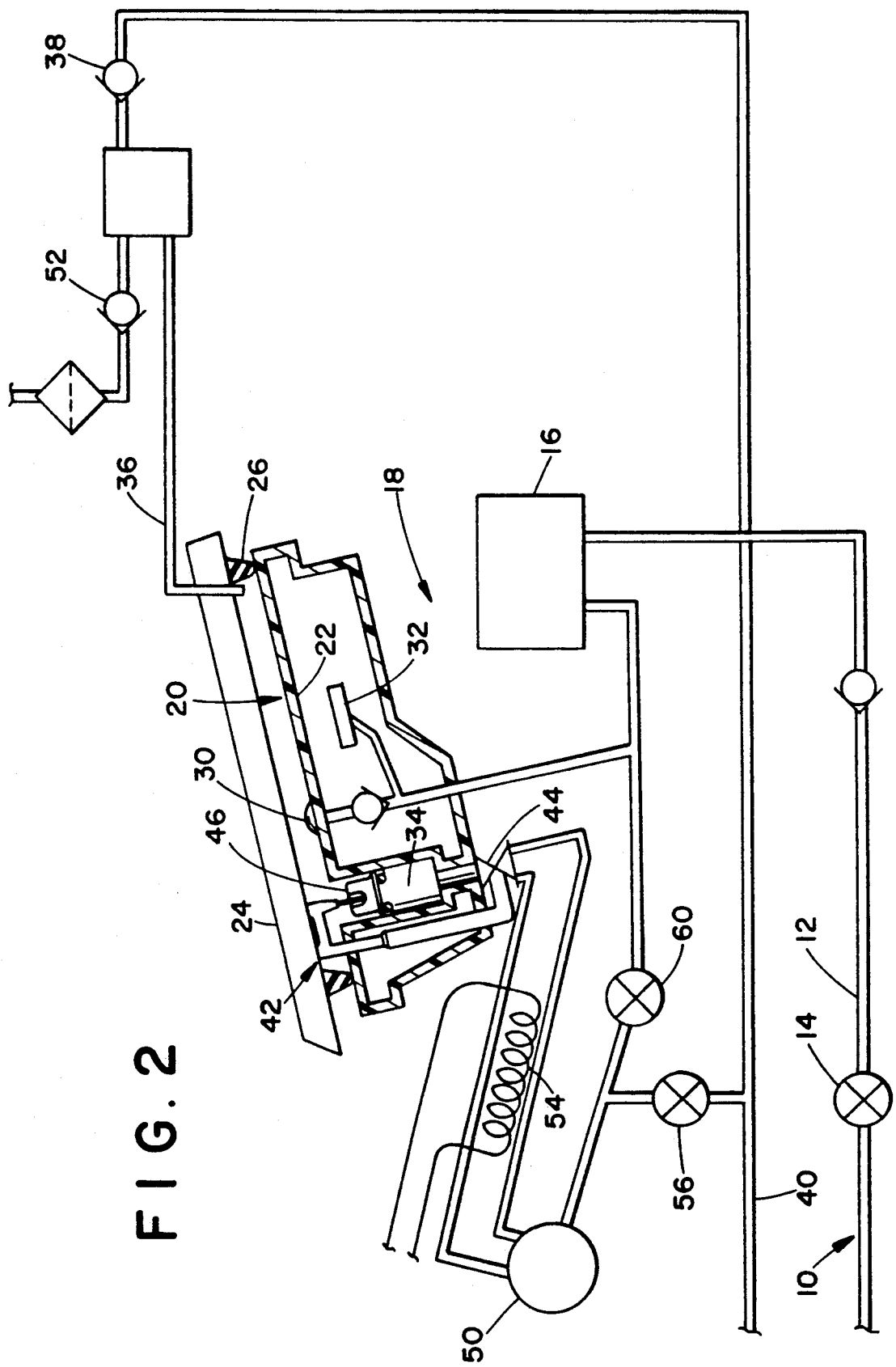

With reference to FIGS. 1 and 2, a dilutant or water source 10 supplies water or other fluid reagents. In the preferred sterilizer embodiment, the water source includes a length of tubing 12 connected with a water spigot or other building plumbing and a control valve 14 for selectively preventing and permitting the flow of water to a sterilizing means 16. In the preferred embodiment, the sterilizing means is a filter which removes particles which are as large or larger than bacteria. Optionally, an in-line water treatment means may be provided for modifying the chemical composition of the water. For example, a water softening cartridge may be provided for reducing or eliminating calcium and magnesium salts from the water. Alternately, various water treatments may be added to the water, such as a wetting agent, a sequestering agent, or others of the reagents to be discussed herein below.

A tubing system 18 connects the filter or sterilizing means with a container or module 20 for receiving an item to be sterilized. In the preferred embodiment, the container is defined by a removable tray 22 configured in accordance with the item, e.g. an endoscope. A lid 24 is sealed to the tray in a lowered position by a resilient gasket 26 to complete the container. Optionally, a transparent window 28 is defined in the lid.

The tubing system includes a spray nozzle 30 and a container distribution manifold 32 for distributing water and other fluids around the item to be sterilized. A reagent receiving well 34 collects the fluid for return. Vent lines 36 enable air to be vented from the container such that it is completely filled with the water or other sterilant solution. Any excess fluid is discharged through check valve 38 into a drain line 40.

A reagent introduction system 42 introduces corrosion inhibitors and anti-microbial agents into the water. Preferably, the corrosion inhibitors are introduced first and circulated over the item to be sterilized or disinfected before the anti-microbial agent. This provides corrosion protection before the corrosive anti-microbial agent contacts the item. Alternately, the corrosion inhibitors and anti-microbial agent may be introduced concurrently such that both reach the item contemporaneously. An aspirator 44 which draws a oxidizing sterilant concentrate or other liquids from an ampule 46. In the preferred embodiment, the oxidant is concentrated peracetic acid which has a stable shelf life of several months. More specific to the preferred embodiment, the operator opens a container having a premeasured dose of powdered reagents and the liquid filled ampule. The powdered reagents are emptied into the well 34 and the ampules positioned to be pierced and drained by the aspirator. As described in greater detail below, the powdered reagents include a buffer, e.g. a phosphate, for bringing the pH to a neutral level and to inhibit steel corrosion. A wetting agent further inhibits pitting of metals. An aluminum corrosion inhibitor, such as a molybdate inhibits aluminum and steel corrosion. A copper and brass corrosion inhibitor, preferably a triazole, protects copper and brass components. Moreover, there is a synergistic interaction in which the phosphates, molybdates, triazoles, and wetting agent interact to protect steel, aluminum, copper, and brass better than if any one were eliminated. If tap water, rather than deionized water is used as the dilutant, a sequestering agent, e.g. sodium hexametaphosphate, is included to prevent the precipitation of its calcium and magnesium salts.

The operator closes the lid and the system is filled with water. A pump 50 selectively draws water from the container 20 through well 34 and aspirator 44. Recirculating the water dissolves the powdered reagents and aspirates the sterilant from the ampule and circulates the sterilant and reagents through the tubing system 18. Preferably, the vent line 36 is very short and of a substantial diameter such that the solution is circulated over exposed surfaces of the drain check valve 38 and a vent check valve 52. A heating coil adjusts the temperature of the solution. Recirculation continues until the interior of the container and all exposed surfaces of the tubing system and valves are sterilized. Alternately, once fully dissolved, the sterilant may remain quiescent for a selected duration.

After the preselected sterilization or disinfecting period, the sterilant solution is drained through a drain valve 56 and sterile air is drawn into the system through an air sterilizing means—preferably a filter that removes any particles the size of a bacteria or larger. The filled valve 14 is opened and the drain valve 56 is closed such that the sterile filter 16 provides a source of sterile rinse. Note that the sterile rinse passes only along sterilized surfaces of the tubing system and valves in order to assure sterility. Every tubing and valve surface from the filter to the drain was exposed to the circulating sterilant solution for a sufficient duration to assure its sterility. The pump 50 circulates the sterile rinse through the system for a selected duration sufficient to rinse salt residue that the buffered strong oxidant tends to deposit. At the end of the rinse cycle, the rinse solution is drained by opening drain valve 56. When a return valve 60 is closed, the pump 50 functions to pump liquid from the system out the drain 40. Additional drain lines (not shown) and aspirators or pumps (not shown) may be provided for removing liquids from every region of the system. The exact location of such additional drains will be dependent on the bends and contours of the plumbing system.

In the preferred embodiment, the ampule contains 35% peracetic acid and appropriate stabilizers, as are known in the art to provide an acceptable shelf life. The volume of the ampule relative to the volume of the tubing system 18 is selected such that the peracetic acid is diluted to about 0.2% by weight per volume solution. However, final solutions of 0.005%-1% may prove acceptable. Other oxidants may also function suitably as an anti-microbial such as phenol, ozone, organic peroxides, hydrogen peroxides, inorganic peroxides and other active oxygen releasing compounds, other oxidants such as chlorine dioxide, chlorine, hypochlorites and active chlorine releasing compounds, such as chloramines. The selected anti-microbial, and its concentration, and the contact time with the item will vary depending on whether disinfection or sterilization is sought. In many applications, only disinfection is sought. The contact time or the strength composition of the anti-microbial agent may be adjusted accordingly.

The copper and brass corrosion inhibitors are preferably benzotriazoles and tolytriazoles, which are preferred due to their stability in the presence of strong oxidizing compounds. Mercaptobenzathiozol might also be utilized but is more apt to be oxidized or destabilized by strong oxidizers.

Azoles, benzoates, and other five membered ring compounds may also prove acceptable as copper and brass corrosion inhibitors.

The anti-corrosive buffering compounds are preferably a mixture of phosphate in sufficient volume to produce a final concentration of 1.25% weight per volume and molybdates in an appropriate amount to produce a final solution of 0.011% weight per volume. Phosphates may also be effective in the range of 0.2% to 12% and the molybdates may be effective from 0.1 to 10%. Optionally, borates, chromates, dichromates, tungsdates, vanadates and combinations thereof, may be substituted in appropriate concentrations to inhibit steel corrosion, i.e. buffer to a generally neutral pH, and aluminum corrosion.

In hard water, the phosphates tend to cause calcium and magnesium salts to precipitate and coat the instruments being sterilized and parts of the sterilizing system. A sequestering agent appropriate to prevent precipitation, such as sodium hexametaphosphate, may be provided. Of course, if deionized or soft water is utilized the sequestering agent may be eliminated. However, to insure universal applicability with any water that might be utilized, the presence of a sequestering agent is preferred.

A wetting agent present to about 0.001 percent (W/V) improves the wetting of the surface of the instrument by the anti-microbial agent. The wetting agent has also been found to increase penetration of the anti-microbials improving anti-microbial efficacy while reducing corrosion.

The following are examples that illustrate the effect corrosion inhibiting effectiveness of various strong oxidant anti-microbial formulations. Particular attention was paid to corrosion of the metals:

Metals
A. Brass
B. Stainless Steel
C. Aluminum
D. Carbon Steel
E. Copper

In the following tables, the degree of corrosion is encoded as follows:
1. No corrosion;
2. Slight corrosion;
3. Moderate corrosion;
4. High corrosion; and,
5. Heavy corrosion.

EXAMPLES

| Exposure Time | A | B | C | D | E |
|---|---|---|---|---|---|
| Base Formula | | | | | |
| 1000 ppm Lithium Hypochlorite | | | | | |
| 0.125% Monosodium Phosphate | | | | | |
| 0.8% 1-H-Benzotriazole | | | | | |
| 0.025% Sodium Hexametaphosphate | | | | | |
| pH 7.9 | | | | | |
| 30 minutes | 1 | 1 | 1 | 1 | |
| 90 minutes | 1 | 1 | 1 | 1 | |
| 65 hours | | 2 | 1 | 2 | 1 |
| Base Formula | | | | | |
| 2000 ppm Peracetic Acid | | | | | |
| 0.125% Monosodium Phosphate | | | | | |
| 1.12% Disodium Phosphate | | | | | |
| 0.08% 1-H-Benzotriazole | | | | | |
| 0.025% Sodium Hexametaphosphate | | | | | |
| 0.05% Sodium Molybdate | | | | | |
| pH 6.4 | | | | | |
| 30 minutes | 1 | 1 | 1 | 1 | 1 |
| 16 hours | 1 | 1 | 1 | 1 | 1 |
| 24 hours | 1 | 1 | 1 | 1 | |
| Base Formula | | | | | |
| 1300 ppm Lithium Hypochlorite | | | | | |
| 0.6% Disodium Phosphate | | | | | |
| 0.52% Monosodium Phosphate | | | | | |
| 0.09% Sodium Molybdate | | | | | |
| 0.07% 1-H-Benzotriazole | | | | | |
| 0.045% Sodium Hexametaphosphate | | | | | |
| 0.009% CO-720* | | | | | |
| pH 7.0 | | | | | |
| 30 minutes | 1 | 1 | 1 | 1 | |
| 1 hour | 1 | 1 | 1 | 1 | |
| Base Formula | | | | | |
| 500 ppm Lithium Hypochlorite | | | | | |
| 1.25% Monosodium Phosphate | | | | | |
| 0.5% Sodium Molybdate | | | | | |
| 0.03% Sodium Hexametaphosphate | | | | | |
| 0.05% CO-720* | | | | | |
| 0.08% 1-H-Benzotriazole | | | | | |
| pH 6.95 | | | | | |
| 30 minutes | 1 | 1 | 1 | 1 | |
| Base Formula | | | | | |
| 500 ppm Lithium Hypochlorite | | | | | |
| 1.25% Monosodium Phosphate | | | | | |
| 1.25% Disodium Phosphate | | | | | |
| 0.5% Sodium Molybdate | | | | | |
| 0.05% Sodium Hexametaphosphate | | | | | |
| 0.08% 1-H Benzotriazole | | | | | |
| 0.3% 2A1** | | | | | |
| pH 6.95 | | | | | |
| 30 minutes | 1 | 1 | 1 | 1 | |
| Base Formula | | | | | |
| 1000 ppm Lithium Hypochlorite | | | | | |
| 1.25% Monosodium Phosphate | | | | | |
| 1.25% Disodium Phosphate | | | | | |
| 1.0% Sodium Molybdate | | | | | |
| 0.08% 1-H-Benzotriazole | | | | | |
| pH 7.0 | | | | | |
| 30 minutes | 1 | 1 | 1 | 1 | |
| 24 hours | 1 | 1 | 1 | 1 | |
| Base Formula | | | | | |
| 1000 ppm Lithium Hypochlorite | | | | | |
| pH 11.2 | | | | | |
| 1 hour | 3 | 3 | 5 | 5 | |
| Base Formula | | | | | |
| 500 ppm Lithium Hypochlorite | | | | | |
| pH 11.0 | | | | | |
| 1 hour | 3 | 3 | 5 | 5 | |
| Base Formula | | | | | |
| 2000 ppm Peracetic Acid | | | | | |
| pH 2.0 | | | | | |
| 1 hour | 5 | 3 | 5 | 5 | |

*CO-720 = Poly(oxy-1,2-ethanediyl),alpha-(nonyphenyl)-omega-hydroxy-$(C_2H_4O)_nC_{15}H_{24}O$ n = 12
**A1 = Dodecyl (Sulphenoxy)benzene sulfonic acid, disodium salt and oxybis (dodecyl benzene sulfonic acid), disodium salt The invention has been described with reference to the preferred embodiments. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiments, the invention is now claimed to be:

1. An anti-microbial solution comprising:
   a strong oxidant selected from the group consisting of organic peroxides, peracids, and chloride releasing compounds;
   a copper and brass corrosion inhibitor;
   a buffering agent;
   at least one anti-corrosive agent which inhibits corrosion in at least aluminum, carbon steel, and stainless steel, the anti-corrosive agent including at least two compounds selected from the group consisting of chromates and dichromates, borates, phosphates, molybdates, vanadates, and tungsdates; and
   a wetting agent, the strong oxidant being present in a sufficient concentration at least to disinfect an item wet with the solution and the corrosion inhibitor and anti-corrosive agent being present in a sufficient concentration relative to the strong oxidant to inhibit the strong oxidant from corroding copper, brass, aluminum, carbon steel and stainless steel elements of the item.

2. The anti-microbial solution as set forth in claim 1 wherein the copper and brass corrosion inhibitor includes a triazole.

3. The anti-microbial solution as set forth in claim 2 wherein the anti-corrosive agent includes at least one compound selected from the group consisting of molybdates, chromates and dichromates, borates, vanadates, tungsdates, and mixtures thereof.

4. The anti-microbial solution as set forth in claim 2 wherein the anticorrosive agent includes a phosphate and at least one of molybdates, chromates, tungsdates, borates, vanadates, and mixtures thereof.

5. The anti-microbial solution as set forth in claim 4 further including a sequestering agent for preventing the phosphate from causing precipitation in hard water.

6. The anti-microbial solution as set forth in claim 1 wherein the copper and brass corrosion inhibitor is selected from the group consisting of triazoles, azoles and benzoates.

7. The anti-microbial solution as set forth in claim 1 further including a sequestering agent.

8. An anti-microbial solution comprising:
   a peracetic acid;
   a copper and brass corrosion inhibitor;
   a buffering agent;
   at least one anti-corrosive agent which inhibits corrosion in at least aluminum, carbon steel, and stainless steel, the anti-corrosive agent including a phosphate and at least one of borates, molybdates, chromates, tungsdates, vanadates, and mixtures thereof; and
   a wetting agent.

9. An anti-microbial solution comprising:
   a strong oxidizing agent including peracetic acid;
   a copper and brass corrosion inhibitor including a triazole;
   a buffering agent;
   at least one anti-corrosive agent including at least two compounds selected from the group consisting of chromates and dichromates, borates, phosphates, molybdates, vanadates, and tungsdates for inhibiting corrosion in at least aluminum, carbon steel, and stainless steel, and
   a wetting agent.

10. The anti-microbial solution as set forth in claim 9 wherein the peracetic acid is present in 0.005%–1% W/V, the triazoles are present in 0.001%–1% W/V and the anti-corrosive agent is present in 0.2%–53%.

11. The anti-microbial solution as set forth in claim 10 wherein the anticorrosive agent includes a phosphate present in the range of 0.2% to 12% (W/V) and a molybdate present in the range of 0.1% to 40% (W/V).

12. The anti-microbial solution as set forth in claim 11 further comprising a sequestering agent.

13. The anti-microbial solution as set forth in claim 12, wherein the peracetic acid is present in 0.2% W/V; phosphate is present in the 1.25% W/V; molybdate is present in about 0.011% W/V; the triazole is present in about 0.008% W/V; the sequestering agent is present in about 0.0027% M/V; and the wetting agent is present in about 0.0011% W/V.

14. An anti-microbial solution for disinfecting instruments, the solution comprising:
   0.005%–1% peracetic acid
   0.001%–1% triazoles;
   0.2%–12.5% phosphates;
   0.01% to 10% of a compound selected from the group consisting of chromates and dichromates, borates, molybdates, vanadates, and tungsdates;
   0%–0.01% sequestering agent; and
   a wetting agent.

15. A method of removing microbial contamination from medical instrument comprising:
   dissolving in water a phosphate, a triazole, a wetting agent, and a compound from the group consisting of chromates and dichromates, borates, molybdates, vanadates, and tungsdates;
   mixing an anti-microbial agent with the water;
   circulating the water, anti-microbial agent, and dissolved compound solution over the medical instrument and interior surfaces of a microbially decontaminated rinse water supply line and extending between a source of the microbially decontaminated rinse water and the instrument and surfaces that are in fluid communication therewith such that all surfaces with which the microbially decontaminated rinse water comes in contact have been microbially decontaminated; and
   rinsing the instrument with the microbially decontaminated rinse water.

16. A method of removing microbial contamination from a medical instrument comprising:
   dissolving in water a phosphate, a triazole, a wetting agent, and a compound from the group consisting of chromates and dichromates, borates, molybdates, vanadates, and tungsdates;
   mixing a concentrated anti-microbial agent which includes peracetic acid with the water;
   circulating the water, anti-microbial agent, and dissolved compound solution over the medical instrument to be microbially decontaminated; and,
   rinsing the instrument with the microbially decontaminated water.

17. An anti-microbial solution comprising:
   a strong oxidant selected from the group consisting of organic peroxides, peracids, chloride releasing compounds, chlorine dioxide, hyperchlorides, and phenol;
   a brass and copper corrosion inhibitor selected from the group consisting of triazoles, azoles and benzoates;
   a buffering agent;

an anti-corrosive agent which includes at least two compounds selected from the group consisting of chromates, dichromates, borates, phosphates, molybdates, vanadates, and tungsdates; and
a wetting agent.

18. An anti-microbial solution for sterilizing medical instruments, the solution comprising:
0.005%–1% peracetic acid
0.001%–1% triazoles;
0.2%–12.5% phosphates;
0.01% to 10% of a compound selected from the group consisting of chromates and dichromates, borates, molybdates, vanadates, and tungsdates;
0%–0.01% sequestering agent; and
a wetting agent.

19. A method of removing microbial contamination from a medical instrument comprising:
dissolving in water a phosphate, a triazole, a wetting agent, and a compound from the group consisting of chromates and dichromates, borates, molybdates, vanadates, and tungsdates;
mixing with the water a concentrated anti-microbial agent of the group consisting of phenol, organic peroxides, and active chloride releasing compounds;
circulating the water, anti-microbial agent and dissolved compound solution over the medical instrument to be microbially decontaminated at least until the instrument is disinfected; and
rinsing the instrument with microbially decontaminated water.

* * * * *